US012588832B2

(12) United States Patent
Brejl et al.

(10) Patent No.: US 12,588,832 B2
(45) Date of Patent: Mar. 31, 2026

(54) MODULAR MOUTHPIECE

(71) Applicant: Exhalation Technology Limited, Cambridge (GB)

(72) Inventors: Stig Lytke Brejl, Cambridge (GB); Roger Yttervik, Cambridge (GB)

(73) Assignee: Exhalation Technology Limited, Cambridge (GB)

( * ) Notice: Subject to any disclaimer, the term of this patent is extended or adjusted under 35 U.S.C. 154(b) by 482 days.

(21) Appl. No.: 18/007,102

(22) PCT Filed: Jul. 28, 2021

(86) PCT No.: PCT/GB2021/051944
§ 371 (c)(1),
(2) Date: Jan. 27, 2023

(87) PCT Pub. No.: WO2022/023743
PCT Pub. Date: Feb. 3, 2022

(65) Prior Publication Data
US 2023/0225631 A1 Jul. 20, 2023

(30) Foreign Application Priority Data

Jul. 29, 2020 (GB) ...................................... 2011756

(51) Int. Cl.
*A61B 5/097* (2006.01)
(52) U.S. Cl.
CPC ...... *A61B 5/097* (2013.01); *A61B 2560/0443* (2013.01)
(58) Field of Classification Search
None
See application file for complete search history.

(56) References Cited

U.S. PATENT DOCUMENTS

| | | | |
|---|---|---|---|
| 5,081,871 A | 1/1992 | Glaser | |
| 2004/0162500 A1 | 8/2004 | Kline | |

(Continued)

FOREIGN PATENT DOCUMENTS

WO 2020053431 A1 3/2020

OTHER PUBLICATIONS

International Search Report and Written Opinion mailed Oct. 14, 2021 in corresponding International Application No. PCT/GB2021/051944.

(Continued)

*Primary Examiner* — Jay B Shah
(74) *Attorney, Agent, or Firm* — Renner, Otto, Boisselle & Sklar, LLP.

(57) ABSTRACT

A mouthpiece is disclosed through which a user inhales and exhales when providing an exhaled breath sample. The mouthpiece includes a mouth-engaging element about which a user places their mouth when using the mouthpiece and also a housing having a housing wall. The housing wall defines a first aperture through the housing wall, the first aperture being linked by a conduit defining a first fluid flow path to the mouth-engaging element. Interposed therebetween is a first directional valve, allowing air into the mouthpiece from atmosphere. A second conduit is provided, defining a second fluid flow path from the mouth-engaging element, and directing exhaled air out of a second aperture of the mouthpiece. The second conduit houses a second directional valve housed within the second fluid flow path.

10 Claims, 13 Drawing Sheets

(56) References Cited

U.S. PATENT DOCUMENTS

| | | | |
|---|---|---|---|
| 2014/0288454 A1 | 9/2014 | Paz et al. | |
| 2016/0245797 A1 | 8/2016 | Ahmad et al. | |
| 2017/0119280 A1* | 5/2017 | Ahmad | A61B 5/0878 |
| 2019/0388007 A1* | 12/2019 | Oki | A61B 5/742 |
| 2020/0041485 A1 | 2/2020 | Funch-Nielsen | |

OTHER PUBLICATIONS

International Preliminary Report on Patentability mailed Oct. 19, 2022 in corresponding International Application No. PCT/GB2021/051944.

* cited by examiner

Mouth piece

10

13

21

20

Pressure connection

Inhalation valve = OPEN ON INHALATION, CLOSED ON EXHALATION valve = CLOSED ON INHALATION, OPEN ON EXHALATION

18

14

13

10

To mouth

Inhalation and exhalation ports can be fitted with valves

61

Inhalation / exhalation chamber

Main body

40

41

62

80

82

83

83

81

83

MODULAR MOUTHPIECE

This application is a national phase of International Application No. PCT/GB2021/051944 filed Jul. 28, 2021, which claims priority to United Kingdom Application No. 2011756.0 filed Jul. 29, 2020, each of which is incorporated herein by reference in its entirety.

FIELD OF THE INVENTION

The invention relates to a mouthpiece for use incorporated into an apparatus to collect and analyse exhaled breath, and especially to a modular mouthpiece. The mouthpiece is particularly suitable for preventing cross-contamination between different users of the apparatus and to any supervising health workers who may be present when a sample of breath is being collected. The mouthpiece can be used in conjunction with devices which function in either or both of a clinical or research environment.

BACKGROUND TO THE INVENTION

Within the health industry it has long been recognised that care needs to be taken when using a diagnostic apparatus with which a patient comes into contact, in that the use of the apparatus by that patient does not lead to contamination both of subsequent samples and of subsequent patients using the apparatus. In the past 6 months this has been especially recognised as a problem as the world deals with the Covid-19 crisis. The need to prevent samples of a pathogen from remaining on a surface of an apparatus and also from being expelled to the atmosphere, usually as part of an aerosol has become particularly acute. Especially difficult is the situation where the apparatus relates to carrying out an analysis of the exhaled breath of a patient, as many pathogens are carried in the aerosol phase of the exhaled breath.

Three main solutions to one or both of the problems can be visualised. The first is to simply prevent contact between the sample and any following patient. This is quite difficult to achieve, especially in respect of measurements with which the current invention is concerned: exhaled breath. The second solution is to ensure that any apparatus is thoroughly cleaned between patients. Care must be taken that the cleaning regime is carried out properly each time. Moreover, the cleaning agents need to be safe for patients to inhale and must not damage components of the apparatus. The third solution is to make a part of the apparatus which may harbour a pathogen disposable.

The present invention is concerned with a disposable mouthpiece for use in apparatus which measures components of exhaled breath of a patient.

A further problem, particularly when dealing with taking samples of exhaled breath is that some of the analytes measured are present to only a small percentage of the overall breath sample obtained. In order to obtain sufficient sample to make measurement feasible, one option is for a large sample to be taken, which is not always possible, particularly if a patient has COPD. Alternatively, the concentration of the analyte in the breath can be increased.

It is a further object of the present invention to provide a mouthpiece which seeks to provide a means of increasing the concentration of an analyte in exhaled breath.

SUMMARY OF THE INVENTION

According to the invention there is provided a mouthpiece through which a user inhales and exhales when providing an exhaled breath sample, the mouthpiece including a mouth-engaging element about which a user places their mouth when using the mouthpiece;

the mouthpiece including a housing having a housing wall, the housing wall defining a first aperture through the housing wall, the first aperture being linked by a conduit defining a first fluid flow path to the mouth-engaging element, and interposed therebetween a first directional valve, allowing air into the mouthpiece from atmosphere, a second conduit, defining a second fluid flow path from the mouth-engaging element, and directing exhaled air out of a second aperture of the mouthpiece, the second conduit housing a second directional valve housed within the second fluid flow path.

The mouthpiece thus provides a means of allowing a user to breath easily from atmosphere without having to disconnect themselves from the device, the device being then able to be disposed of safely, including the valves which would in normal usage become contaminated and be difficult to clean.

Optionally a filter is interposed between the first aperture and the mouth-engaging element to filter particulate material out of the inhaled air and preventing the particulate material from reaching the user.

Preferably, a directing wall is provided located on the outside of the housing wall, and further preferably surrounding the first aperture.

The mouthpiece preferably includes a chamber module, optionally secured about the directing wall, the chamber module defining an atrium and having one or more ports to allow inhaled and/or exhaled breath to enter and leave the mouthpiece. Optionally, the atrium includes a dividing wall separating inhaled and exhaled breath.

The mouth-engaging element is optionally removable allowing the mouth-engaging element to be replaced, so improving hygiene.

BRIEF DESCRIPTION OF THE DRAWINGS

The invention is now described with reference to the accompanying drawings which show by way of example only, one embodiment of a mouthpiece. In the drawings.

DETAILED DESCRIPTION OF THE INVENTION

Figures 1A, 1B:
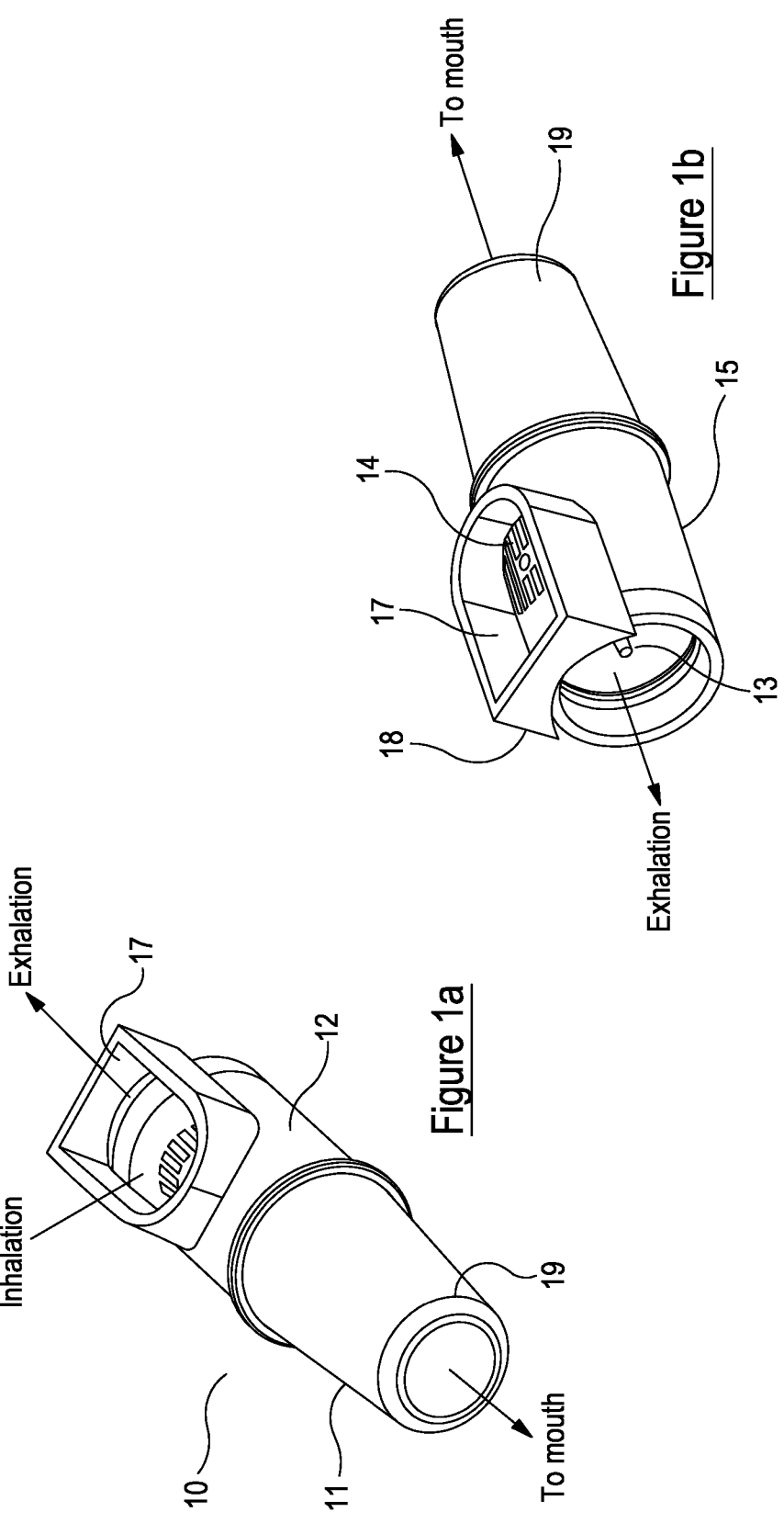
FIGS. 1*a* and 1*b* are perspective images of a first embodiment of mouthpiece.

In its broadest aspect, the present invention relates to an integrated mouthpiece intended to be used with breath collection and breath analysis systems. The mouthpiece can contain one or more valves which, by virtue of their being open or closed, direct airflow along a pre-determined path. The path which the inhaled and exhaled breath follows is driven by a set of directional valves. The logic of the valves can be such that when one subset is open another subset may be closed. Whether a valve is set to the open or closed configuration is determined by the required direction of the air flow. The mouthpiece can contain two or more chambers which are connected by one or more valves. In prior art devices, although disposable mouthpieces are known, the incorporation of the valves into the mouthpiece means that one aspect of a breath collection device, the flow control valves, which is likely to become most contaminated, is not used by different patients, thereby reducing the risk of cross-contamination.

In one embodiment the air is inhaled though the mouthpiece and an inhalation valve opened to allow air from atmosphere into the device and subsequently into the lungs of the patient. Upon exhalation the inhalation valve is closed, and a second valve opened to allow the exhaled air to travel into a second chamber of the mouthpiece, now made accessible by the opening of this second valve. Alternatively, the exhaled air can be directed directly into another device to which the mouthpiece is fluidly and/or physically connected.

The mouthpiece is preferably provided with a fitment means to enable the mouthpiece to mate with a second device. The fitment means can be a pressure fitting, a screw fitting, a bayonet fitting etc. The fitment means provided is sufficiently tight that air does not leak excessively from the mating between the mouthpiece and the second device To decrease the risk of cross-contamination between individual patients, a mouthpiece is intended to be used by a single patient. The mouthpiece construction, therefore, and materials used in the construction are such that the mouthpiece can be discarded after use. The materials of construction can be a polymeric material such as a plastics material or a ceramic, but also can be formed from biodegradable materials such as paper, card and specifically biodegradable polymers etc.: biocompatible and biodegradable materials are preferred.

The mouthpiece is intended to be used in breath collection and breath analysis devices. In order to protect people in the vicinity of the test such as healthcare workers from breath-borne pathogens, the exit ports can include filters onboard to filter pathogens from being vented into the ambient air.

The mouthpiece is intended, in a preferred mode of use, for a single patient use and is intended to be disposed of after a patient's use. This disposal can be done in a sealable bag/container. Into the container/sealable bag can be introduced an anti-pathogen reagent, for example hydrogen peroxide; which anti-pathogen is intended to reduce the biological hazard involved in disposing of such a device.

The design of the mouthpiece is such that the restriction of air-flow to the patient is minimised during inhalation, so that the mouthpiece allows a patient to carry out normal tidal breathing. This means that the mouthpiece can be used by patient who would not otherwise be able to perform forced air movements, such as patient with COPD.

The connection means between the mouthpiece device and the second device, be the second device a breath collection or breath analysis device or combination of the two, is made so that the total volume of air within is minimized. The total internal volume of the mouthpiece can be less than 500 cm$^3$. This means that a single exhalation should clear any residual previous breath from the device, including clearing the dead space. The mouthpiece can be used in conjunction with a 'shield', which is intended to further isolate the patient from the device which they are using.

In a further embodiment, the mouthpiece allows a partial recycling/re-circulation of air of a particular patient's breath. This means that a portion of the exhaled breath maybe inhaled and exhaled several times, which acts to increase the concentration of a breath analyte within the gas and vapour phase, within the device. The partial recycling avoids the risk, which would be present should the entire breath, solely, be inhaled of the oxygen content becoming eventually too low and the carbon dioxide content too high. For tests where the usual concentration of an analyte of interest is low, for example that of hydrogen peroxide in the case of chronic inflammatory disease, or virus detection on the breath the analytes of pathogen, sample can be concentrated within the breath phase in the device which improves the limits of detection in a consequent detection method. The principles within this device can be extended to molecules in the gas phase including nitric oxide/fractionated nitric oxide.

The mouthpiece can be manufactured as a single piece or can be of a modular design where two or more separate pieces come together to form the overall device. A modular design allows for designs not achievable in a single piece to be constructed. The modular design also allows for customisation of a single module to fit an application or instrument, whilst leaving the other modules as standard items. This modularity means that the device can be adopted by the general breath collection and breath analysis industry, as modules that mate to third party instruments can be customized whilst leaving the overall device intact.

Turning now to the figures, the invention will be described in more detail.

The invention can relate to a single integrated mouthpiece device through which air can be inhaled and exhaled, the device can contain one or more valves whose placement allows the route of inhalation of breath to be different from the path of breath exhalation. The device performs all the necessary functions involved within the workflow of inhaling and exhaling of the breath without manual interference, apart from the placements of the patient's lips around the device forming the seal between the device and mouth. In a preferred embodiment of the device the inhalation port/valve is connected to the patient's mouth by a short flow path.

Following exhalation, the exhaled breath is guided to an exit port by the closing of the inhalation valve and the opening of the exhalation valve, these valves can be passive in that they are one-way valves that are able open to allow air to flow only in one direction, and so close when air attempts to flow in the opposite direction. Diaphragm valves would be an example of such valves. In one embodiment the mouthpiece is a two-chamber device, where air can be inhaled into a first chamber and then into the lungs. Subsequently upon exhalation the breath moves back into the first chamber. A second valve then opens to allow air into a second chamber and thence to an attached breath instrument.

The mouthpiece can have one or more filters which filter the exhaled air to remove particulates and or pathogens from the patient from freely flowing to atmosphere.

The mouthpiece is intended to be used with a second device where either or both of the breath condensate being collected and/or analysed is carried out. When the mouthpiece is used with a second device the mouthpiece functions irrespective of whether the breath's gas phase, aerosol phase or vapour phase is to be collected or analysed. The dimensions of the device facilitate normal tidal breathing.

The mouthpiece can be connected to a second device by a push fit connection, threaded parts etc. The mouthpiece is independent of the second part, but the second device could be a breath analyser or breath collection system or a combination of the two.

The air vents through a filter are designed to prevent harmful material originating from the patient being vented into the atmosphere. The mouthpiece is intended to be used by a single patient and not shared between patients. It may be possible to decontaminate the part so that different patients can use the mouthpiece, but this is not a preferred mode of use, as decontamination can never be guaranteed, and a small risk of cross-infection always remains.

Ideally the device is used by a single patient and then disposed of. The device is constructed from one or more of a set of materials that facilitate clean/sterile assembly, but also assist in the safe and environmentally compatible mode of disposal. Materials of construction includes polymers, card, paper etc.

Upon disposal, a disposing receptacle can be provided into which the used mouthpiece is placed, within the receptacle is a means to release/add a sterilising material, such as a bleach, oxidant, surfactant etc.

In an embodiment of the device where there are two chambers separated by a non-return valve, the breath is inhaled through a first chamber, whilst the breath is exhaled out through both chambers, i.e. the first chamber and a second chamber. The two chambers are separated by a valve which means that the breath is filtered, to remove larger particulates as the exhaled breath is passed from the first chamber to the second chamber. Specifically, saliva and material from the mouth is caught within the first chamber and at the valve, so only air and breath vapour reaches the second chamber and subsequently enters the breath measurement device.

In an alternative embodiment the air within the device can be recycled with the air in the lungs, and with each recirculation of the air, the concentration of analyte or pathogen within the breath phase of the device will increase.

The device within this invention provides a means by which a sample of breath can be inhaled and exhaled, and the exhaled fraction is delivered to a different outlet from the original inlet. This divergence of breath inhalation and breath exhalation is achieved by one or more valves. The device is sized so that the device can be received comfortably in the mouth and allowing patients to perform normal tidal breathing. The mouthpiece is optionally provided with a generic fitment such that the mouthpiece can be attached to a number of different instruments for breath collection and analysis. The device is designed so as not to put the patient at risk, including infection risks, and is also designed so that it can be safely disposed of. Further the mouthpiece can be used with a shield to further isolate the patient from a device being used in conjunction with the mouthpiece.

In the simplest embodiment the mouthpiece can connect to a single second device, but in other embodiments it is possible to have multiple parallel devices all connected to the same mouthpiece using a form of splitter or manifold. The exhaled breath can be sent to more than one device either sequentially or in parallel, depending on how the valves are arranged and timed. When the mouthpiece is attached to more than one device the breath can be sent to the second device in a proportionate or disproportionate way, for example flow restrictors can be used to divert air flow to one device preferentially to another device.

In further embodiments it is possible to have active devices within the mouthpiece such as valves, or to include sensors such as temperature, flow, and humidity.

In FIG. 1 is illustrated a first embodiment of a mouthpiece. In the illustration the flow path of the inhaled air through the mouthpiece is different from the flow path followed by exhaled air. This divergence in flow paths is achieved in this embodiment by two valves having the reverse logic to each other i.e. when one valve is open the other is closed.

The mouthpiece, generally referenced 10, shown in FIG. 1 is a two-chamber device, the two chambers being separated by a non-return valve. During the inhalation phase air enters the first chamber 11 through the entrance 17, and via an inhalation valve, whilst at the same time, the second chamber 12 is isolated by a closed non-return exhalation valve 13. The outer surface 19 of the free end of the chamber 11 can be profiled to enable a user to easily place their mouth about the chamber 11 and so be able to exhale into the device. In the illustrated embodiment, the outer surface 19 has a frusto-conical shape to assist the user. Alternatively, the outer surface 19 can optionally be fitted with a suitably profiled extension. The inhalation valve is in fluid contact with atmosphere by a grille 14 formed in the cylindrical wall 15 of the mouthpiece 10. In the exhalation phase, the inhalation valve closes and the exhalation valve 13 to the second chamber then opens allowing the exhaled air to pass through the first chamber 11 to the second chamber 12. A wall 18 surrounds the opening of the grille 14 to the inhalation valve. In a further embodiment, a filter is optionally placed beneath the grille 14 to prevent particulate material from entering into the mouthpiece 10 on inhalation.

Figures 2A, 2B:
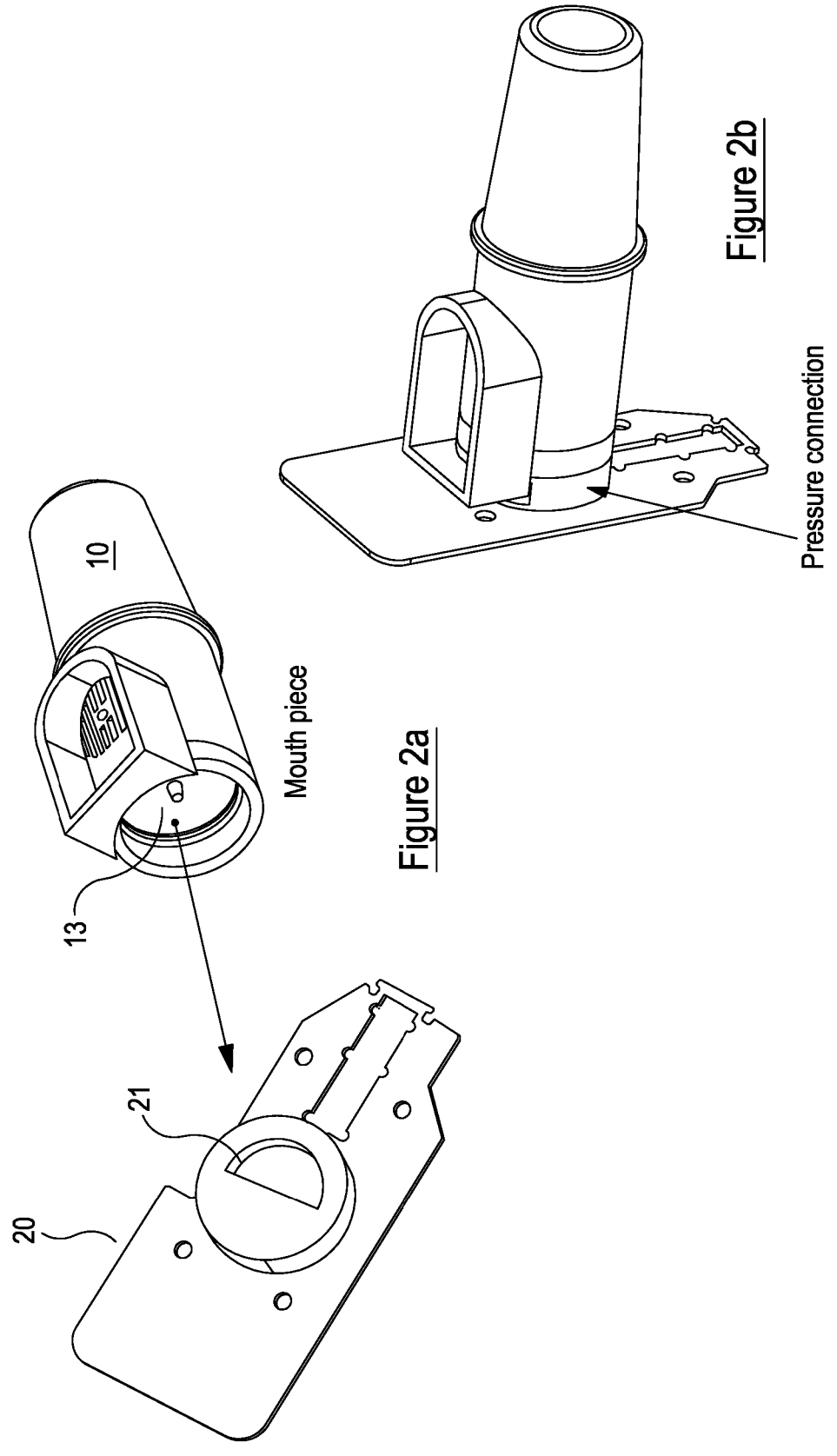
FIGS. 2*a* and 2*b* are perspective images of, respectively, connection of the mouthpiece of FIGS. 1, connected to a sample collector, and the connected components.
Figure 3:
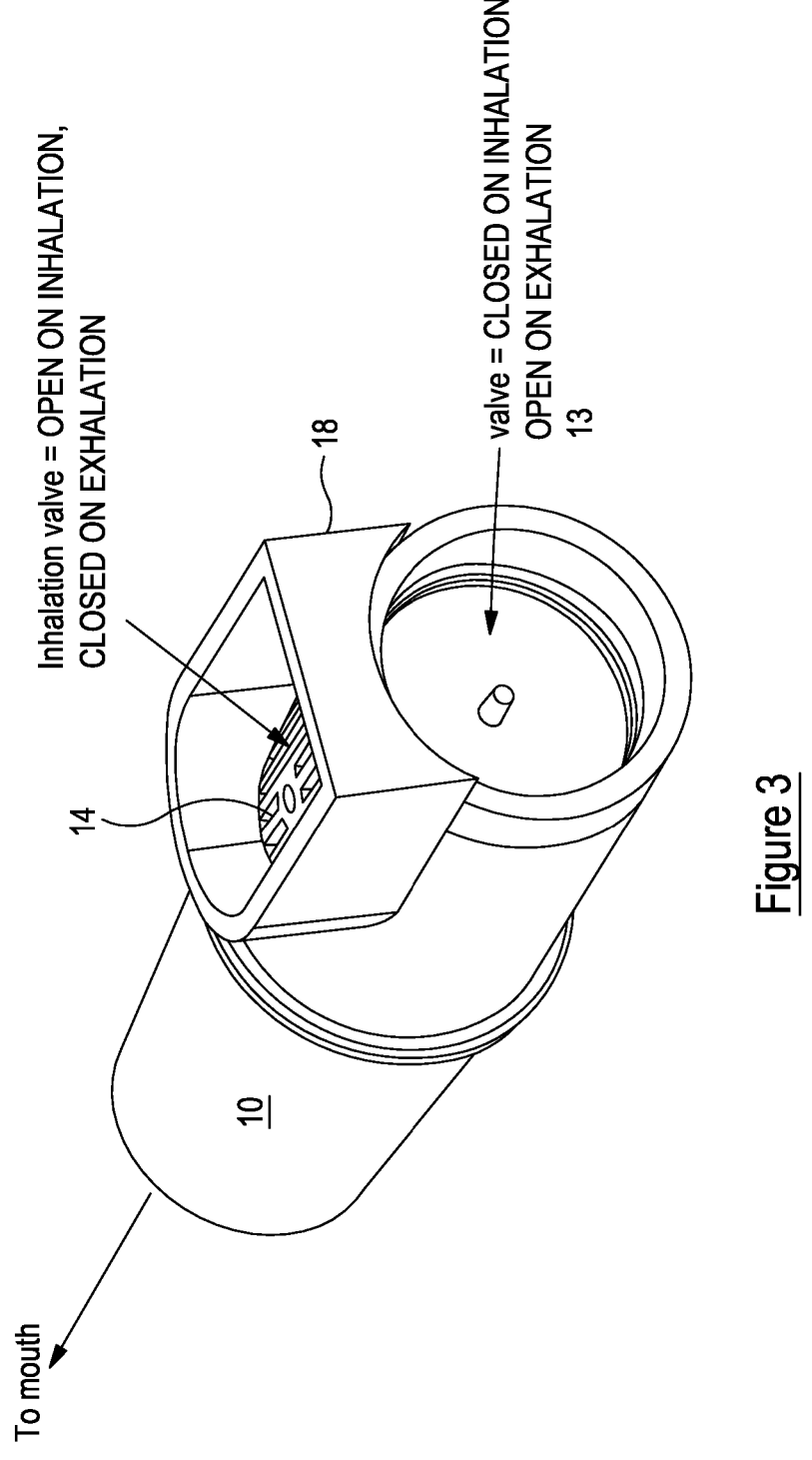
FIG. 3 is a further perspective view of the first embodiment of mouthpiece.

In FIG. 2 is shown an embodiment in which the mouthpiece 10 is connected to an analysis device, in the form of a cartridge analysis device 20 on which breath is collected and analysed. Connection in this example is by means of a push fit connection, although other means known in the art such as through screw fittings, clips etc. can be used. Typically, the cartridge analysis device 20 includes a cooled collection plate on which exhaled breath condenses. The breath exiting the mouthpiece 10 via the valve 13 passes through the aperture 21 and onto the collection plate. Once condensed, the breath flows, for example via microfluidic channels, to analysis regions on the cartridge analysis device 20.

Figure 4:
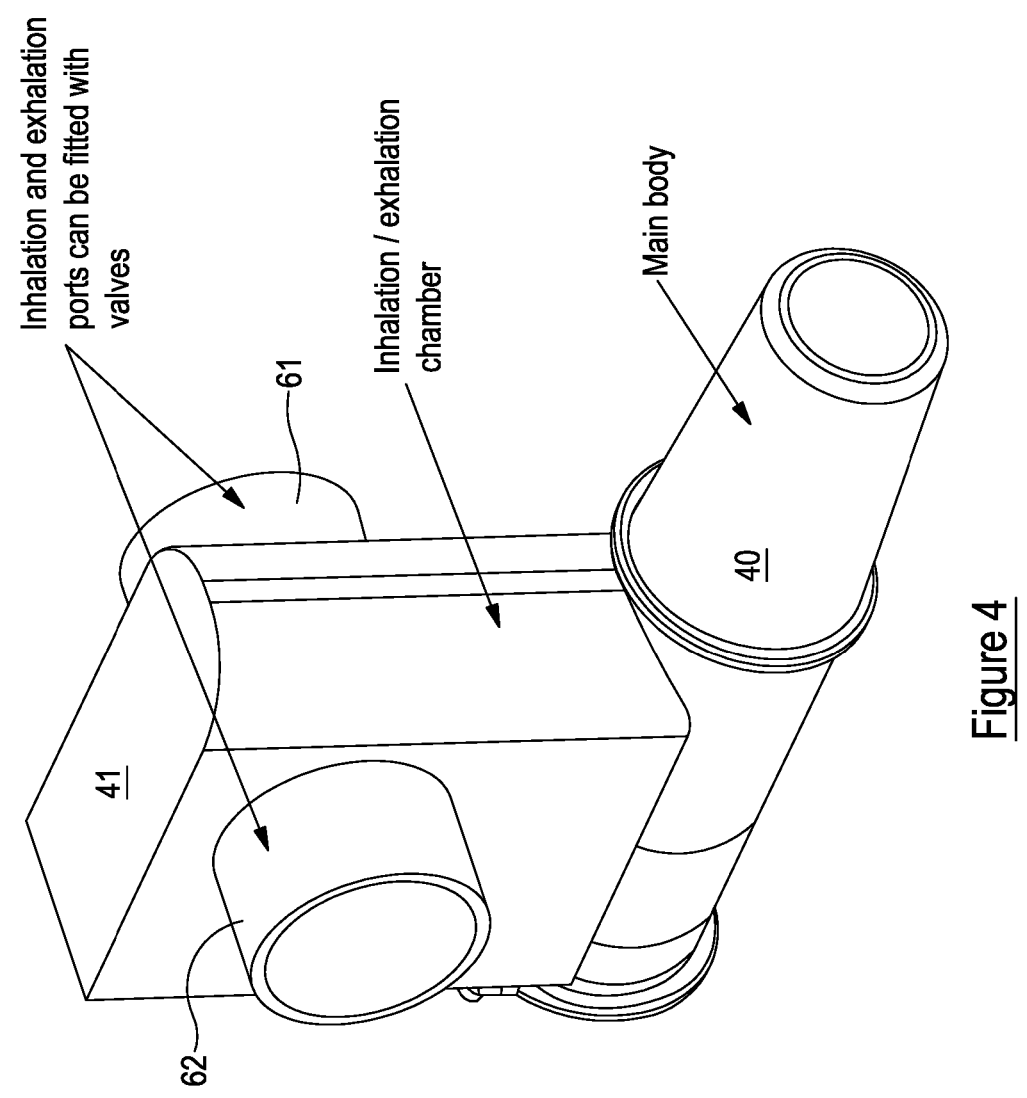
FIG. 4 is a perspective view of a second embodiment of mouthpiece, connected to an inhalation/exhalation chamber.
Figure 6:
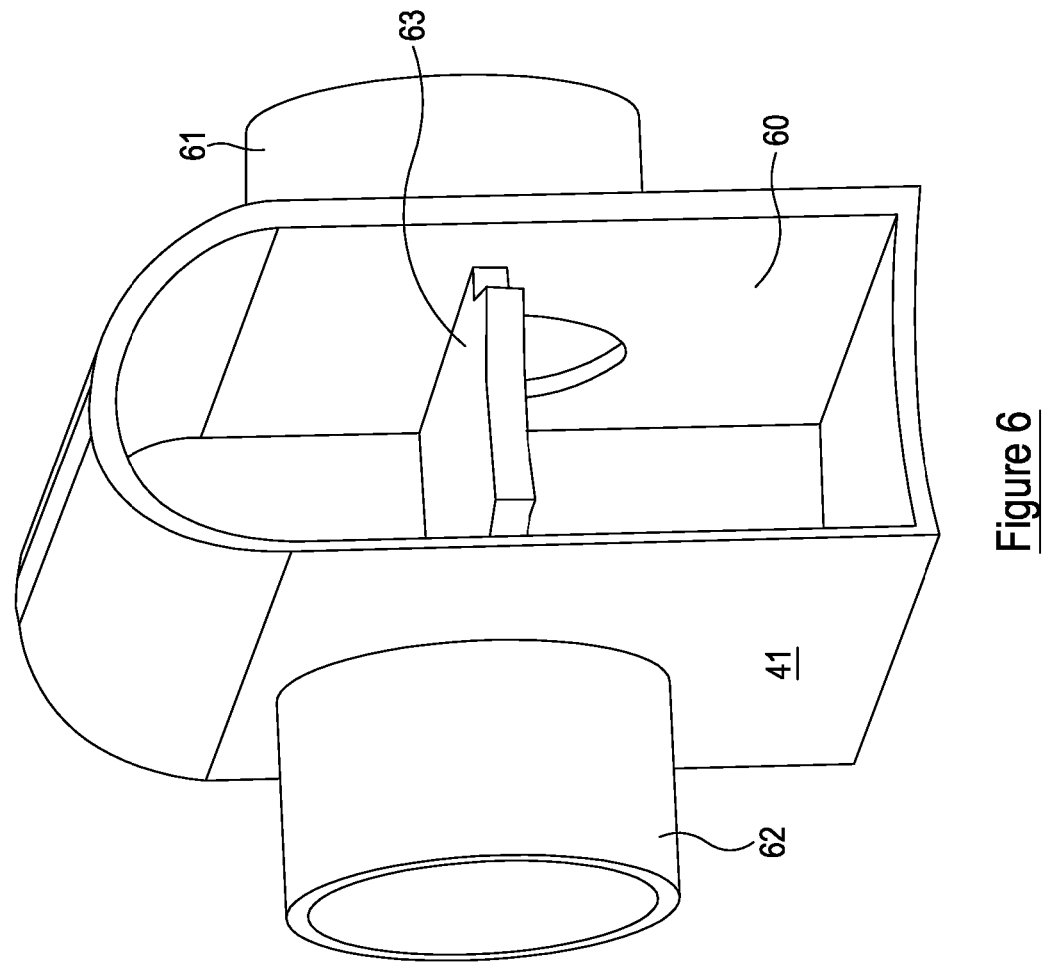
FIG. 6 is a perspective view of a portion of the inhalation/exhalation chamber of FIG. 4.

In FIG. 4 is illustrated an embodiment in which an inhalation/exhalation chamber module 41 has been placed onto the main body of a second embodiment of mouthpiece 40. The chamber module 41 provides the facility to filter either or both of the inhaled and/or the exhaled breath. The chamber module 41 is seated, in a frictional fit, about the wall 18 on the mouthpiece 40, although other fitment means known in the art can be used. The chamber module 41 defines an atrium 60 (see FIG. 6) through which the breath flows. The chamber module 41 is provided with a first, inhalation, port 61, in fluid connection with the inhalation port of the mouthpiece 40. A second, exhalation, port 62 is in fluid connection with atmosphere to prevent the build-up of pressure within the mouthpiece 40 which would interfere with the consistency and reproducibility of samples taken. Both the inhalation and exhalation ports 61, 62 can be provided with filters to prevent unwanted materials such as particulates, viruses, from entering or leaving the mouthpiece.

In this embodiment the atrium 60 is divided by an internal wall 63, which diverts the inhaled and exhaled air to follow different paths through the mouthpiece 40.

Figure 5:
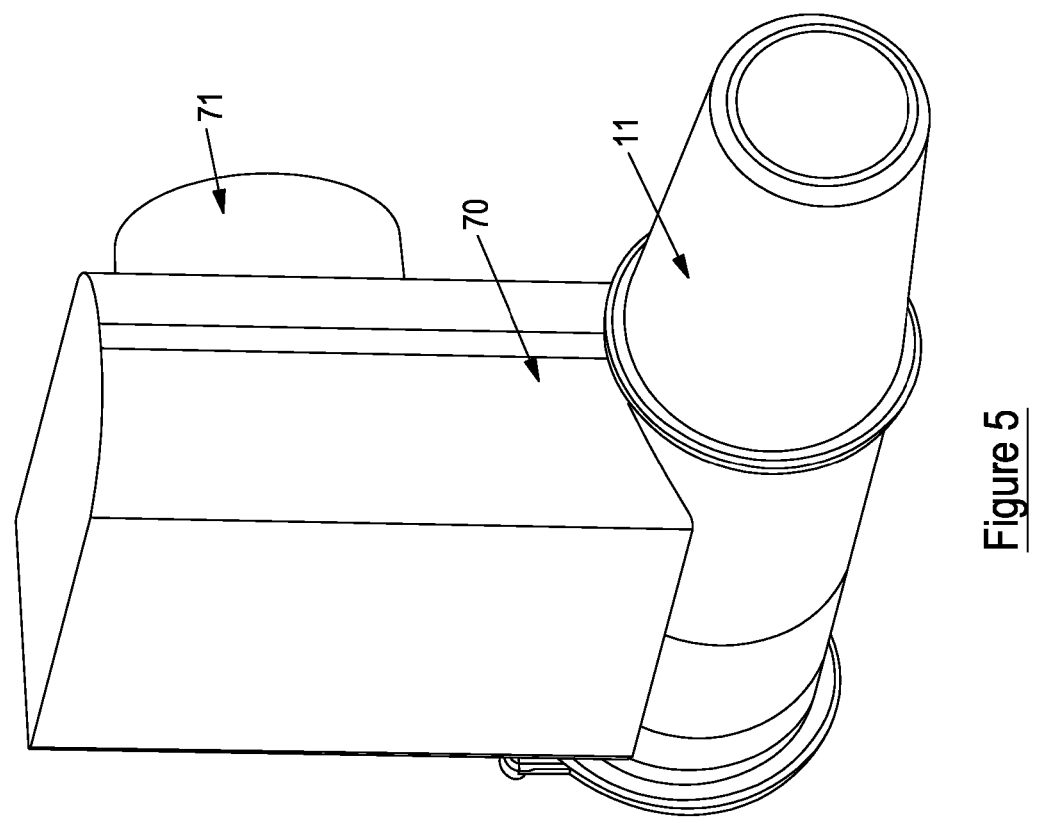
FIG. 5 is a perspective view of the mouthpiece of FIG. 4, connected to a further embodiment of an inhalation/exhalation chamber.
Figure 7:
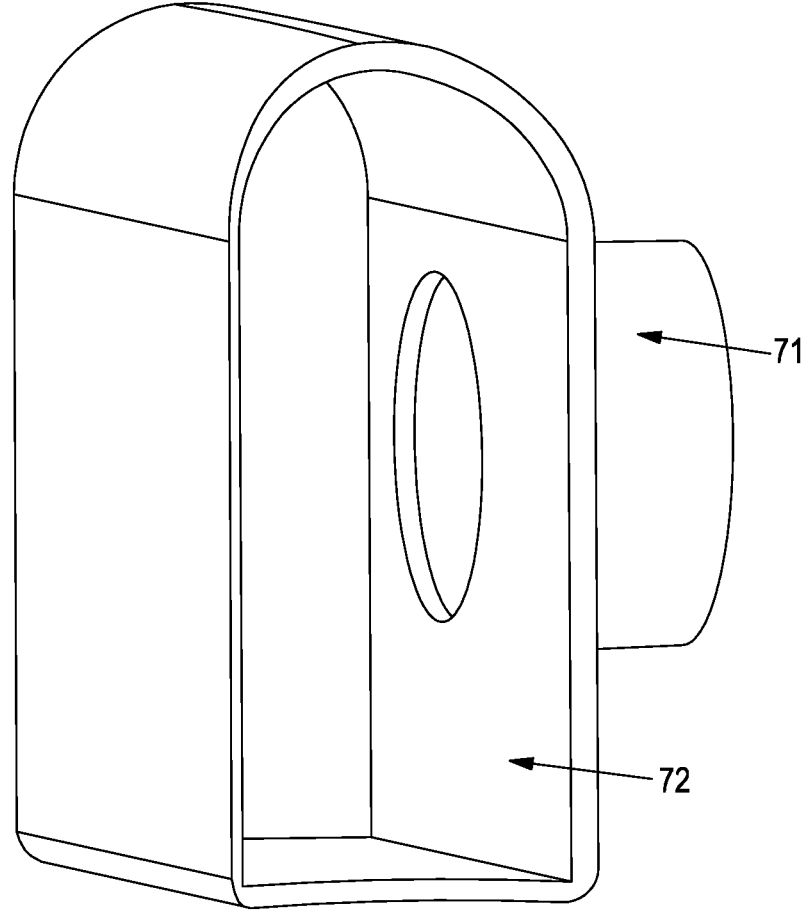
FIG. 7 is a perspective view of a portion of the inhalation/exhalation chamber of FIG. 5.
Figures 8A, 8B, 8C, 8D, 8E:
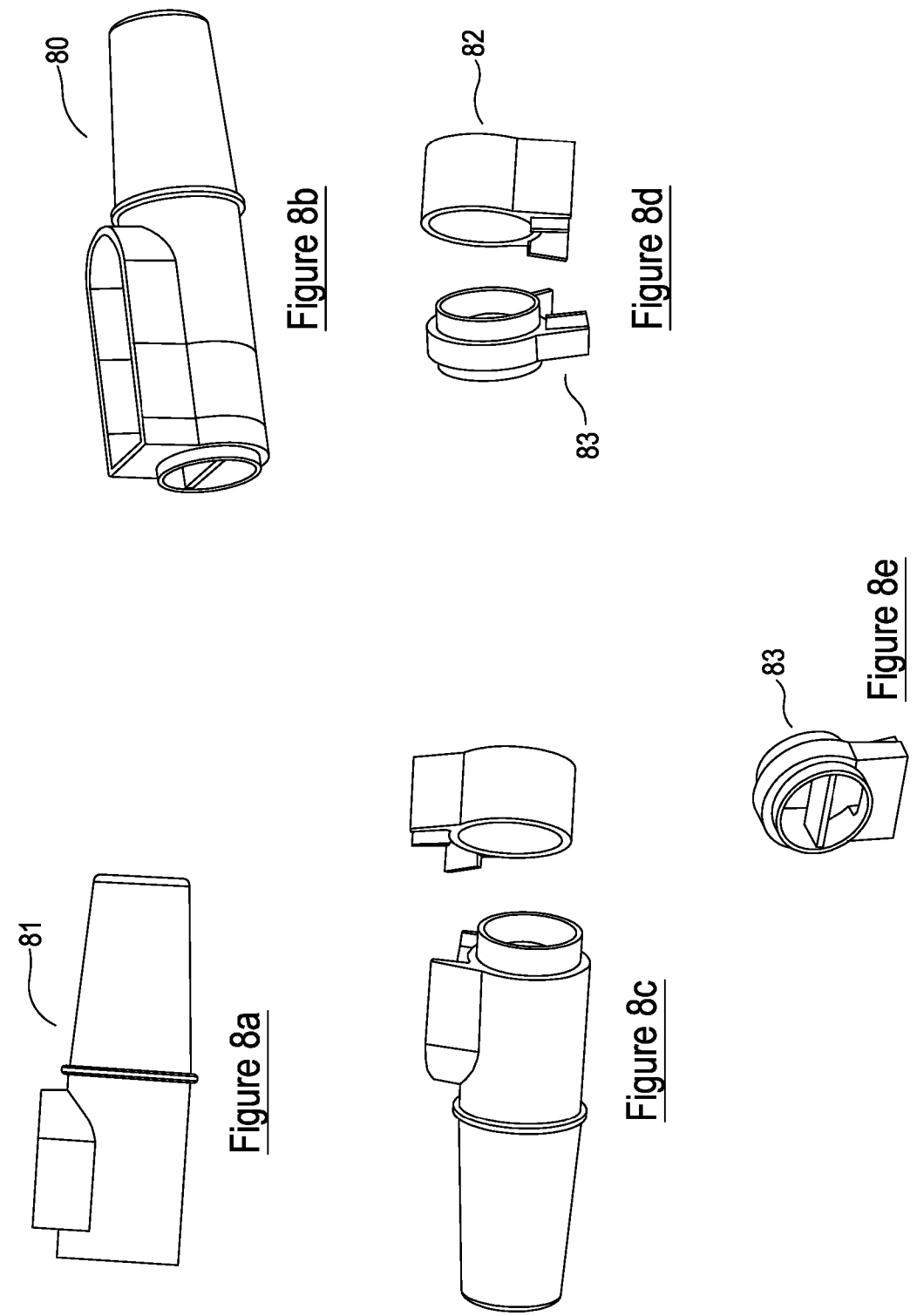
FIG. 8*a*-8*e* illustrate a third embodiment of mouthpiece together with a connector piece.

FIGS. 5 and 7 illustrate a chamber module 70 which has only a single port 71 which functions as both an inhalation and an exhalation port, with the air-flow direction being controlled by an inhalation/exhalation valve. Moreover, there is no internal wall within the atrium 72 of the chamber module 70. In this non-walled embodiment, there is at least partial mixing of inhaled and exhaled air.

In order to provide the above-described functionality, the embodiments of mouthpiece and chamber modules can be provided either as a single, integral item or also in a plurality of sub-sections which can be assembled on site and, if required and safe to do so, disassembled for cleaning and re-use. When provided as a plurality of sub-sections, the sub-sections can be optionally fitted with a push-fit connection or bonded together, with a suitable adhesive, to form the entire device.

In FIGS. 8*a*-8*e* is shown a mouthpiece 80 constructed from three sub-sections 81, 82, 83. The sub-sections 81, 82, 83 are so constructed that when mated together they form a tight seal to prevent unwanted and/or mis-directed air-flow out of the mouthpiece 80. It is intended that the sub-sections can be secured together preferably without the need for tools or adhesives etc., with hand-strength being sufficient to construct the device. A modular design can be of advantage when producing and assembling component parts, such as injection moulding of parts or installation of valves. However, other design methodologies can be used to address these aspects.

Though not encouraged, a mouthpiece can be demountable enabling the mouthpiece to be shipped in a dismantled form, which may help with shipping costs. In another scenario the mouthpiece can be dismantled following use and cleaned. It will be recognised that where cleaning is carried out, this is done in a hygienic manner with care being taken that any contamination on the mouthpiece is not spread. The mouthpiece can therefore be provided in materials which allow the mouthpiece to be cleaned in a standard industrial autoclave apparatus often found in hospital environments. The modules can also be designed so that they cannot be dismantled without breaking, rendering reassembly impossible.

Figure 9:
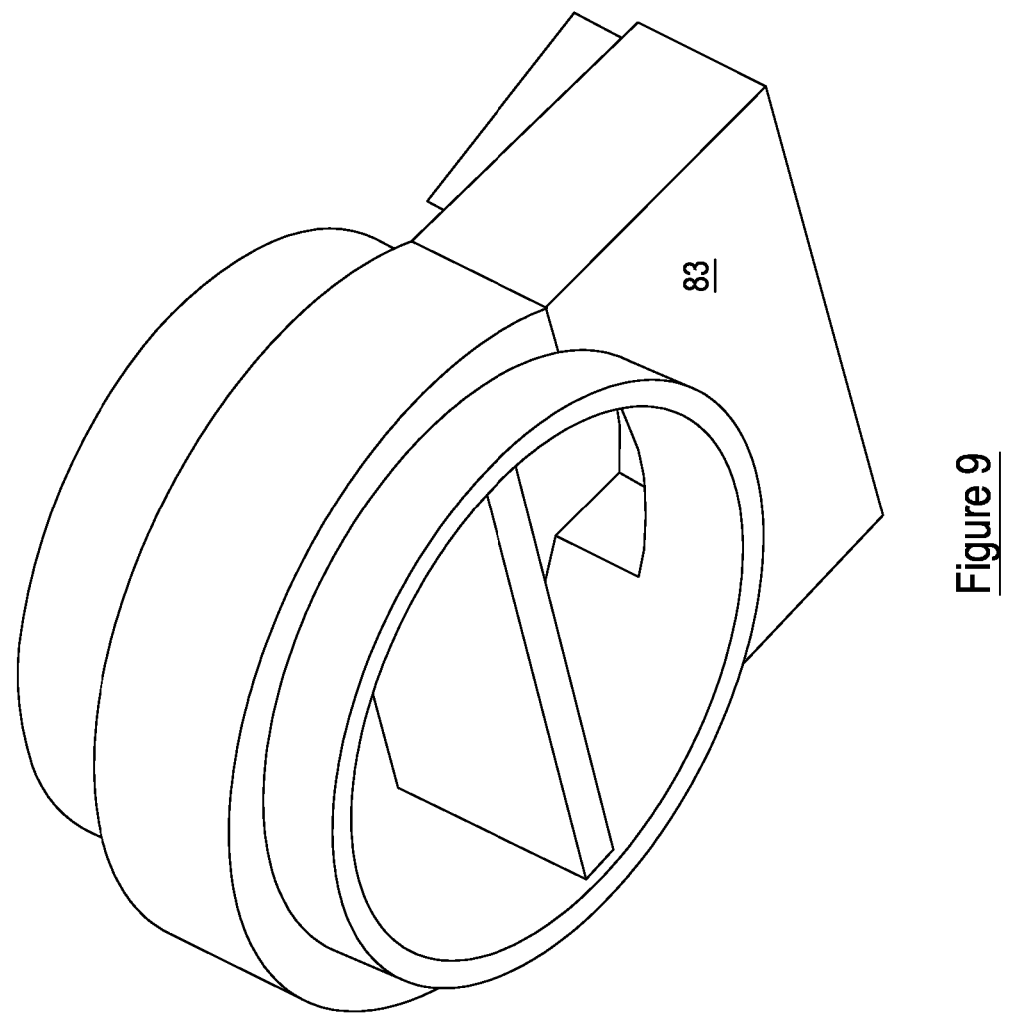
FIG. 9 is a perspective view of the connector piece of FIG. 8.
Figure 10B:
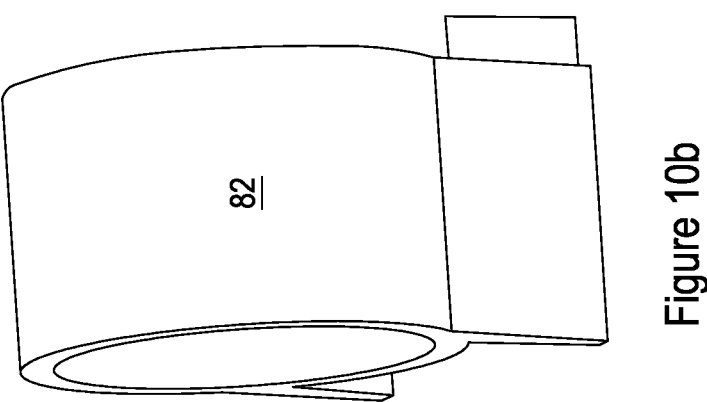
FIGS. 10*a*, 10*b* are further views of the connector piece of FIG. 9.
Figure 10A:
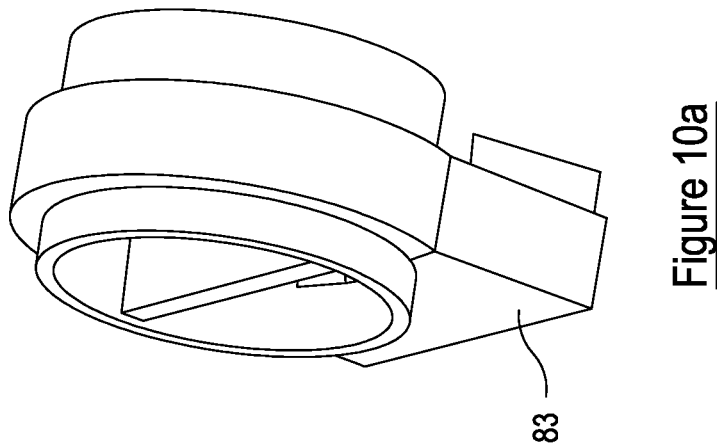
Figure 11:
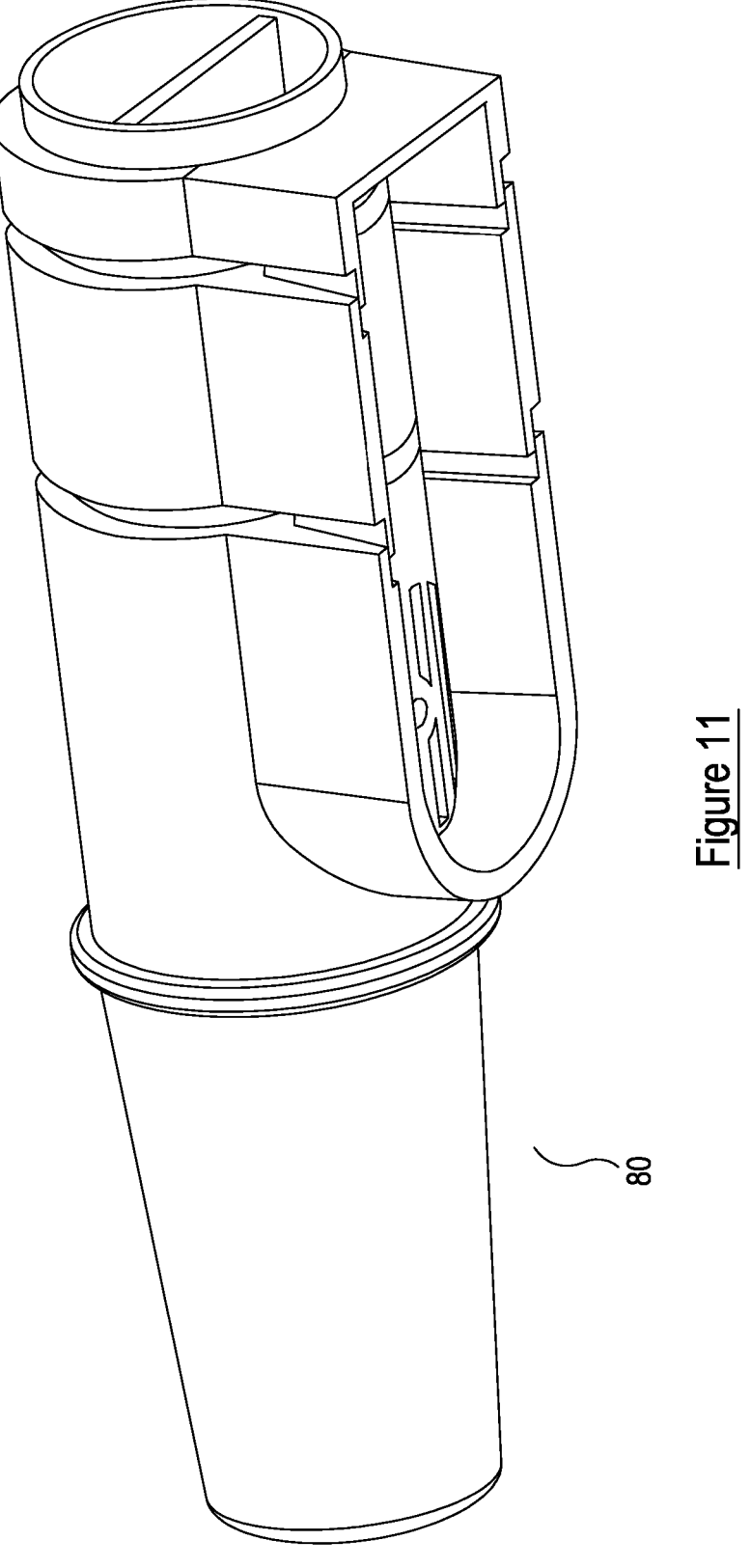
FIGS. 11-13 are further views of the third embodiment of mouthpiece.
Figure 12:
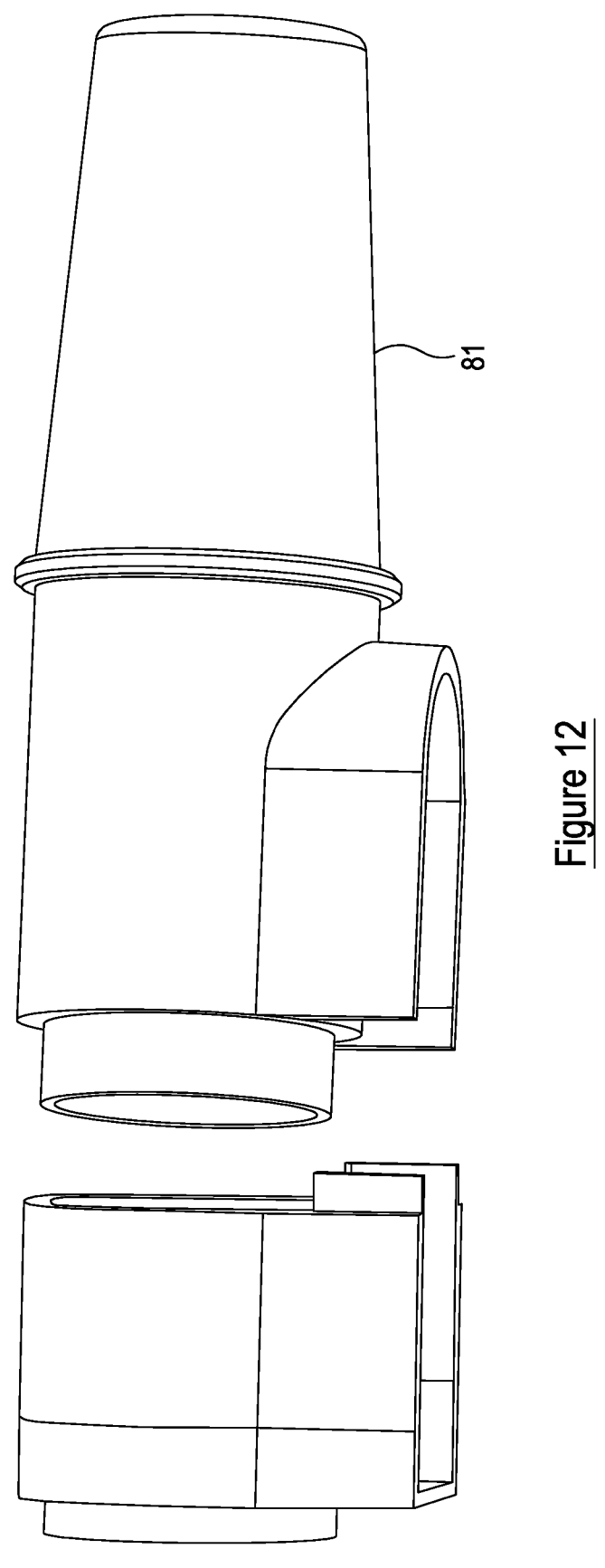
Figure 13:
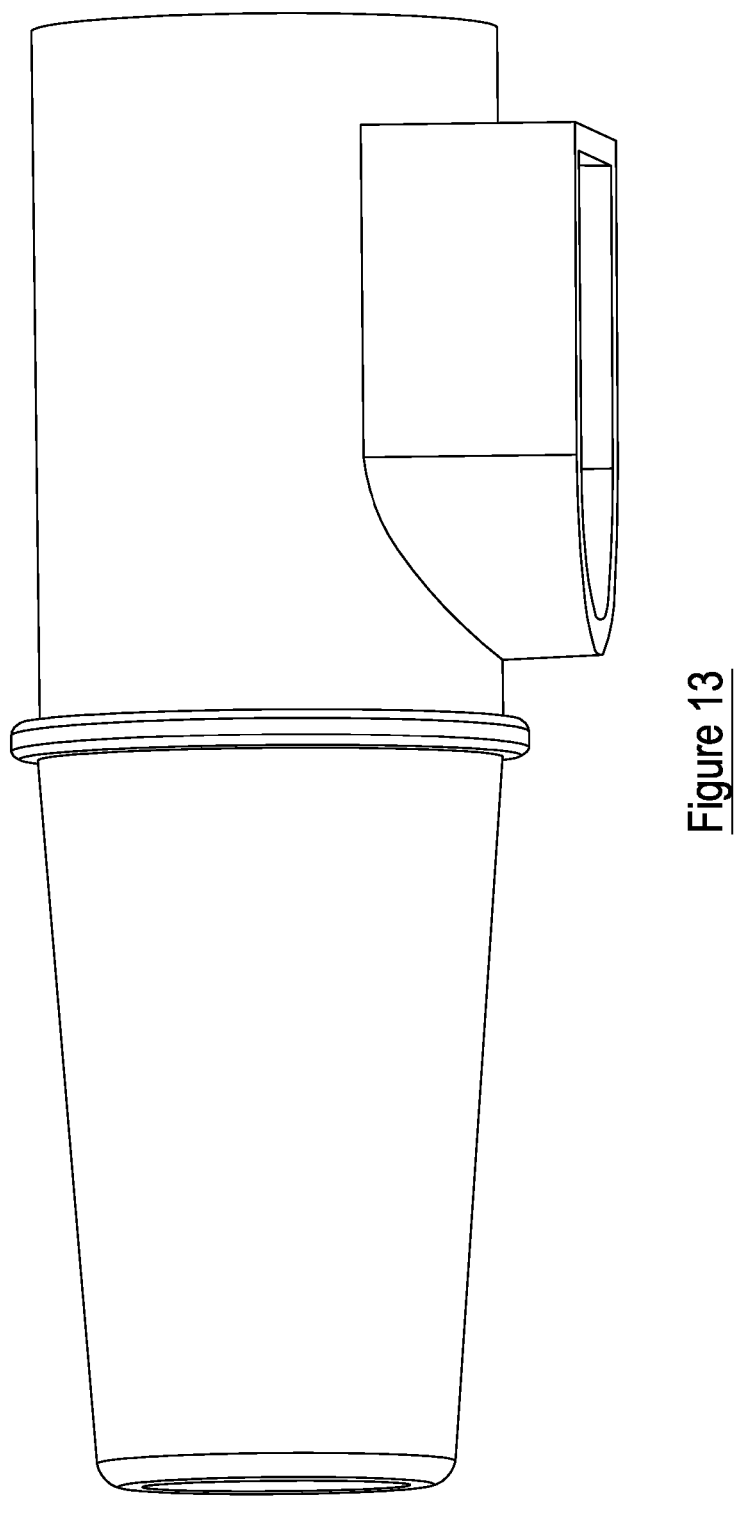

Finally, a mouthpiece in accordance with the above described embodiments can be used with third party breath analysis or breath collection devices or devices that are a combination of the two. The modularity of the device allows customisation of one of more of the modules to fit the third-party device or application. For example, in a mouthpiece having two or more sub-sections, one or more modules can be provided as a standard element, whilst additional modules would be custom parts. For example, in FIG. 9, the component can be customized so that exhaled air passage narrows to a flow channel 1 mm high therefore ensuring the efficient cooling and condensing of exhaled breath condensate when connected to the third-party device.

The invention claimed is:

1. A mouthpiece through which a user inhales and exhales when providing an exhaled breath sample, the mouthpiece including a mouth-engaging element about which a user places their mouth when using the mouthpiece;

the mouthpiece including a housing having a housing wall, the housing wall defining a first aperture through the housing wall, the first aperture being linked by a conduit defining a first fluid flow path to the mouth-engaging element, and interposed therebetween a first directional valve, allowing air into the mouthpiece from atmosphere, a second conduit, defining a second fluid flow path from the mouth-engaging element, and directing exhaled air out of a second aperture of the mouthpiece, the second conduit housing a second directional valve housed within the second fluid flow path wherein a filter is interposed between the first aperture and the mouth-engaging element.

2. The mouthpiece according to claim 1, wherein a directing wall is provided located on the outside of the housing wall.

3. The mouthpiece according to claim 2, wherein the directing wall surrounds the first aperture.

4. The mouthpiece according to claim 1, wherein the mouthpiece includes a chamber module.

5. The mouthpiece according to claim 4, wherein the chamber module is secured about the directing wall, the chamber module defining an atrium and having one or more ports to allow inhaled and/or exhaled breath to enter and leave the mouthpiece.

6. The mouthpiece according to claim 5, wherein the atrium includes a dividing wall separating inhaled and exhaled breath.

7. The mouthpiece according to claim 1, wherein the mouthpiece includes a chamber module, the chamber module defining an atrium and having one or more ports to allow inhaled and/or exhaled breath to enter and leave the mouthpiece.

8. The mouthpiece according to claim 7, wherein the chamber module is secured about the directing wall.

9. The mouthpiece according to claim 7, wherein the atrium includes a dividing wall separating inhaled and exhaled breath.

10. The mouthpiece according to claim 1, wherein the mouth-engaging element is removable from the housing.

\* \* \* \* \*